United States Patent [19]

Milstein et al.

[11] Patent Number: 5,670,547
[45] Date of Patent: Sep. 23, 1997

[54] MOISTURIZING VEHICLE FOR TOPICAL APPLICATION OF VITAMIN A ACID

[75] Inventors: Elliott A. Milstein, West Bloomfield; Nathan Milstein, Hazel Park, both of Mich.

[73] Assignee: Dow Pharmaceutical Sciences, Petaluma, Calif.

[21] Appl. No.: 430,154

[22] Filed: Apr. 26, 1995

Related U.S. Application Data

[63] Continuation of Ser. No. 296,083, Aug. 25, 1994, abandoned, which is a continuation of Ser. No. 951,938, Sep. 25, 1992, abandoned, which is a continuation of Ser. No. 697,527, Apr. 29, 1991, abandoned, which is a continuation of Ser. No. 335,144, Apr. 17, 1989, abandoned.

[51] Int. Cl.$^6$ .................................................. A61K 31/07
[52] U.S. Cl. ........................ 514/725; 514/844; 514/847
[58] Field of Search ...................................... 514/725, 844, 514/847

[56] References Cited

U.S. PATENT DOCUMENTS

| | | | |
|---|---|---|---|
| 3,729,568 | 4/1973 | Kligman | 514/559 |
| 3,906,108 | 9/1975 | Felty | 514/560 |
| 3,934,028 | 1/1976 | Lee | 424/318 |
| 4,073,291 | 2/1978 | Marvel et al. | 12/155 |
| 4,186,207 | 1/1980 | Zeidler et al. | 424/284 |
| 4,214,000 | 7/1980 | Papa | 424/289 |
| 4,256,763 | 3/1981 | McHugh | 424/286 |
| 4,310,509 | 1/1982 | Berglund | 424/28 |
| 4,323,557 | 4/1982 | Rosso et al. | 424/28 |
| 4,424,234 | 1/1984 | Alderson et al. | 514/784 X |
| 4,428,933 | 1/1984 | King | 424/93 |
| 4,443,442 | 4/1984 | Skillern | 424/246 |
| 4,454,159 | 6/1984 | Musher | 424/358 |
| 4,581,380 | 4/1986 | Shroot et al. | 514/700 |
| 4,588,744 | 5/1986 | McHugh | 514/470 |
| 4,591,501 | 5/1986 | Cioca | 424/28 |
| 4,603,146 | 7/1986 | Kligman | 514/559 |
| 4,615,633 | 10/1986 | Ser et al. | 401/196 |
| 4,649,040 | 3/1987 | Pitha | 424/10 |
| 4,666,941 | 5/1987 | Shroot et al. | 514/569 |
| 4,677,120 | 6/1987 | Parish et al. | 514/549 |
| 4,690,775 | 9/1987 | Schott et al. | 252/312 |
| 4,699,929 | 10/1987 | Mustakallio et al. | 514/680 |
| 4,717,720 | 1/1988 | Shroot et al. | 514/63 |
| 4,727,088 | 2/1988 | Scott et al. | 514/725 |
| 4,786,436 | 11/1988 | Ogunbiyi et al. | 252/352 |
| 4,826,828 | 5/1989 | Wilmott et al. | 514/63 |
| 4,826,871 | 5/1989 | Gressel et al. | 514/438 |

FOREIGN PATENT DOCUMENTS 0219208   4/1987   European Pat. Off. .

OTHER PUBLICATIONS

Sales brochure and produce description of colladerm gel moisturizer manufactured by C & M Phramacal, Inc., Hazel Park, Michigan, U.S.A.

*Primary Examiner*—Theodore J. Criares
*Attorney, Agent, or Firm*—Needle & Rosenberg, P.C.

[57] ABSTRACT

A formulation containing tretinoin, a gelling agent, proteinaceous material, and water is provided for the uniform topical application of tretinoin. The water-based formulation is oil- and fat-free, alcohol-free, and rich in proteinaceous material. The formulation is stable over time and is comedogenic and less irritating and drying to the skin.

22 Claims, No Drawings

MOISTURIZING VEHICLE FOR TOPICAL APPLICATION OF VITAMIN A ACID

This application is a continuation of application Ser. No. 08/296,083, filed Aug. 25, 1994 now abandoned; which is a continuation of Ser. No. 07/951,938, filed Sep. 25, 1992, abandoned; which is a continuation of Ser. No. 07/697,527, filed Apr. 29, 1991, abandoned; which is a continuation of Ser. No. 07/335,144, filed Apr. 17, 1989, abandoned.

BACKGROUND OF THE INVENTION

The present invention relates to a topical dosage formulation of tretinoin in which the active ingredient tretinoin is contained in a stable, oil- and fat-free, alcohol-free, and potentially moisturizing vehicle. This product is particularly advantageous for treating such dermatological disorders as acne vulgaris, although it will be understood that this formulation is effective generally for treating dermatological conditions where tretinoin is indicated.

Tretinoin (Vitamin A acid) has been applied topically, (Beer, Yon P., "Untersuchungen über die Wirkung der Vitamin A-Säure," Dermatological, 124:192–195, March, 1962 and Stüttgen, G., "Zur Lakalbehandlung yon Keratosen mit Vitamin A-Säure," Dermatological, 124:65–80, February, 1962) in those hyperkeratotic disorders which are responsive to high oral doses of Vitamin A. Tretinoin, or all trans-retinoic acid, has the following chemical structure:

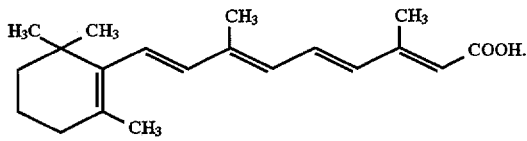

It has been previously demonstrated that prolonged topical application of Vitamin A acid is effective in the treatment of acne (Kligman, A. M., "Topical Vitamin A acid in Acne Vulgaris," Arch Derm., 99:469–476 April 1969). U.S. Pat. No. 3,729,568 to Kligman utilizes a composition in which Vitamin A acid is dispersed in a water-miscible liquid carrier having high solvating action. The carrier used by Kligman consists of a combination of (A) from about 25 to about 75%, by weight, of ethyl alcohol or isopropyl alcohol, and (B) the balance essentially a liquid glycol above ethylene glycol or a liquid glycol above ethylene glycol and a liquid ethylene glycol mono methyl or mono ethyl ether. The topical application of this Vitamin A acid composition causes irritation of the skin in the treated areas.

More recently, it has been found that acne can be effectively treated with a cream formulation containing tretinoin, or Vitamin A acid. A cream formulation is generally more acceptable to patients than the liquid vehicle from the point of view of aesthetics and ease of application. Moreover, another important advantage of the cream form of tretinoin is that it reduces the side effects normally associated with topical application, such as erythema, stinging and itching. These side effects may be sufficient to cause the patient to discontinue the application of tretinoin before it can be fully effective upon the acne.

Notwithstanding these advantages, cream formulations containing tretinoin possess some undesirable attributes. One of these undesirable attributes is the difficulty in uniformly applying sufficient amounts of the active ingredient to the lesion of acne to be effective and at the same time avoid local excesses, surface spread or pooling into facial creases, the nasolabial folds and corners of the mouth where the cream may cause erythema, stinging and itching. Another undesirable attribute of cream formulations of tretinoin is their relative instability, often necessitating the use of refrigeration or special additives to maintain physical and chemical stability over time.

U.S. Pat. No. 3,906,108 to Felty discloses an improvement in stability over previous cream formulations of tretinoin by the addition of xanthan gum to the preparation. The cream consists essentially of a stabilized cream emulsion formulation generally comprising from about 0.005% to about 0.5% by weight of tretinoin; from about 0.1% to about 1.0% by weight of xanthan gum; from about 1% to about 10% by weight of an emulsifier, preferably a non-ionic emulsifier; from about 15% to about 50% by weight of a combination of at least one normally liquid and at least one normally solid hydrophobic material selected from the fatty acids, fatty alcohols and fatty acid esters wherein the fatty acid moiety has from about 12 to about 20 carbon atoms, and pharmaceutical grades of waxes and hydrocarbons (liquid and solid); between about 0.05% and 0.75% by weight of a preservative which prevents bacterial growth in the cream; and from about 0.01% to about 1.0% by weight of an antioxidant, the balance being water. Felty relies upon the use of various fats and oils to provide a carrier for the active ingredient tretinoin.

U.S. Pat. No. 4,247,547 to Marks discloses the use of the gelling agent hydroxypropyl cellulose as a carrier in a preparation containing tretinoin. Marks discloses a formulation for topical application comprising from about 0.01% to about 0.025% by weight of tretinoin and a vehicle system consisting essentially of (a) from about 84 to about 99% by weight of an organic solvent selected from the group consisting of ethanol, isopropanol, and propylene glycol; (b) an effective amount of a pharmaceutically acceptable antioxidant soluble in organic solvent to inhibit oxidation of tretinoin; and (c) an effective amount of hydroxypropyl cellulose to cause gelling. Marks retains the use of organic solvents in his vehicle and claims that the vehicle composition allows for more uniform and effective delivery of tretinoin to the skin with enhanced stability.

As discussed, these previous topical tretinoin formulations have employed a number of methods for the administration of tretinoin in a controlled fashion. Cream emulsion formulations were found to be generally more acceptable to patients than a liquid vehicle, but had the problem of uniformly applying sufficient amounts of the active ingredient to the lesion of acne without local excesses, surface spread or pooling into facial creases and folds, or pooling into the corners of the mouth. In addition, cream formulations contained various fats and oils that tended to form a physical barrier between the tretinoin and the skin surface, thus inhibiting ready absorption of the tretinoin. Methods of administration utilizing liquid solvents tended to be non-uniform in their application of the active ingredient in that they were found to be hard to control when applied to a vertical surface such as the face, i.e. the applied liquid would easily spill off the face, especially when applied liberally. Therefore, there exists a need for a formulation capable of uniformly delivering an effective amount of tretinoin to the surface of the skin in a way which allows for ready absorption by the skin.

Previous cream formulations of tretinoin have utilized hydrophobic materials consisting of various fats and oils to provide a carrier for the active ingredient tretinoin. These hydrophobic materials have included solid and liquid fatty acids, fatty alcohols, fatty acid esters and other hydrophobic materials such as petrolatum, wax, lanolin and mineral oil. The fats and oils contained in these preparations have been found to be comedogenic over time, thereby having an adverse effect on the treatment of acne. This was found to be especially true when the preparations had been used over an extended period of time, which is frequently the clinical case. Therefore, there also exists a need for a formulation that is fat- and oil-free so as to be less comedogenic to the skin with use.

A number of alcohol-based preparations for the topical application of tretinoin have appeared, most of which have proved irritating to the skin at the site of application. This was especially found to be true of applications containing at least 0.025% of tretinoin, in which the astringent side effects of dryness and irritation had prompted discontinuation of use. Since many clinicians wanted the capability of delivering greater than 0.025% of tretinoin to the site of acne, the alcohol-based preparations presented a major obstacle in this regard. Therefore, there exists a further need for a formulation that is alcohol-free so as to be less drying and irritating to the skin with use.

Past cream formulations of tretinoin have encountered problems with physical and chemical stability over time, often requiring the addition of stabilizers or refrigeration. U.S. Pat. No. 3,906,108 to Felty describes the previous to the use of xanthan gum as a stabilizer. Therefore, there exists a further need for a formulation which possesses good physical and chemical stability over time.

One of the possible side effects of topical tretinoin use is the potential for skin drying and irritation. This effect may be severe enough to cause the patient to discontinue the application of tretinoin before it can be fully effective upon the acne, thereby eliminating the chance of any beneficial treatment plan. Therefore, there exists a further need for a formulation which contains a humectant so as to aid in moisturizing the skin and to thus avoid a potential side effect of tretinoin use.

Many of the organic solvents used in previous topical preparations of tretinoin are known to be drying and irritating to skin if applied frequently. The use of a water based preparation, on the other hand, would allow for maintenance of normal skin turgor and consistency by providing a moisturizing action. Therefore, there exists a still further need for a formulation which is water-based so as to avoid the harsh effects of irritating organic solvents.

SUMMARY OF THE INVENTION

The present invention relates to a semisolid dosage formulation used for the uniform topical application of tretinoin. The formulation comprises tretinoin, a gelling agent for uniformly delivering the tretinoin to the surface of the skin in a way which makes it readily absorbable, proteinaceous material for stabilizing the gelling agent, and water. Additional ingredients of the formulation may include, but are not limited to, an antioxidant, a preservative, a surfactant, and glycerin.

The formulation of the present invention provides for the uniform topical application of an effective amount of tretinoin to the skin in a semisolid vehicle which is non-irritating, non-drying and non-comedogenic. The tretinoin is accurately delivered to the surface of the skin and is readily absorbed. The formulation, being water-based and containing proteinaceous material, has a potential moisturizing effect which helps counter the drying side effects of tretinoin use. The formulation is stable over time and requires no additional stabilizers or refrigeration to maintain its chemical and physical stability. The formulation is also oil- and fat-free and therefore less comedogenic than creams during heavy and prolonged use. The formulation of the present invention thus allows for greater amounts of tretinoin to be applied to the skin over time, since the side effects of the tretinoin and vehicle are minimized.

It is therefore the object of the present invention to provide a formulation capable of uniformly delivering an effective amount of tretinoin to the surface of the skin in a way that allows for ready absorption by the skin.

It is also the object of the present invention to provide a formulation that is fat-free and oil-free so as to be less comedogenic to the skin with use.

It is a further object to provide a formulation that is alcohol-free so as to be less drying and irritating to the skin with use.

It is another object of the present invention to provide a formulation which possesses good physical and chemical stability over time.

It is another object to provide a formulation which contains humectants so as to aid in moisturizing the skin and to thus avoid a potential side effect of tretinoin use.

It is still another object of the present invention to provide a formulation which is water-based so as to avoid the harsh effects of irritating organic solvents.

DETAILED DESCRIPTION OF THE PREFERRED EMBODIMENT

A formulation of the present invention, in general, comprises tretinoin, a gelling agent for uniformly delivering the tretinoin to the surface of the skin in a way which makes it readily absorbable, proteinaceous material for stabilizing the gelling agent, and water. Additional ingredients of the formulation may include, but are not limited to, an antioxidant, a preservative, a surfactant, and glycerin.

The concentration of tretinoin in the formulations of the present invention preferably lies within a range of about 0.001% by weight to about 0.5% by weight, the range most likely to be encountered in clinical practice. The tretinoin may, however, be present in the formulation at any effective amount so long as the integrity of the other components of the formulation are not jeopardized.

The gelling agent employed in the formulations of the present invention should be water-soluble and acceptable for use in pharmaceutical preparations. The purpose of the gelling agent is to provide a semisolid formulation for the uniform delivery of tretinoin to the surface of the skin, thus making it readily absorbable. The gelling agent also needs to be of uniform consistency and proper viscosity, allowing the user to easily disperse the active ingredient evenly over acne-affected areas. Furthermore, the gelling agent must be water-soluble, since the use of harsh organic solvents (i.e. ethanol, isopropanol, propylene glycol) needed with non-water-based gelling agents has a detrimental effect on the skin. One such gelling agent that has been found to be extremely effective in the formulations of the present invention is an acidic carboxy polymer, such as Carbomer 940 or Carbopol 940 available from B.F. Goodrich Chemical Co., Cleveland, Ohio. This gelling agent is very stable and effective within a pH range of 5.2 to 5.5, and is used in the present invention with a neutralizing agent to maintain pH, since the viscosity of the acidic carboxy polymer drops off precipitously at a pH less than 5.2. Potential neutralizing agents include organic amines, such as triethanolamine.

The proteinaceous material which may be used in the present invention includes proteins, polypeptides, peptides, amino acids, mucopolysaccharides, or mixtures thereof. The protein is preferably collagen or elastin, although many other proteins well known is the art may be used. An acceptable mucopolysaccharide is sodium hyaluronate. The proteinaceous material in the present invention functions as (1) a stabilizer for the water-based gelling agent preventing breakdown of the gel structure over time and (2) a humectant for the skin countering the drying side effects of tretinoin. Proteins have the additional function of acting as protein-replenishing agents for damaged skin.

The use of water, preferably purified, in the formulations of the present invention is necessary to the functioning of the tretinoin vehicle. The water-based vehicle, containing no fats or oils, provides a formulation which is non-comedogenic and is actually moisturizing to potentially dry skin due to tretinoin use. In addition, the use of a water-based vehicle eliminates the necessity to completely solvate the tretinoin in a solvent to deliver it to the skin, as tretinoin is effectively delivered in a uniform fashion with the use of a water-based gel.

An antioxidant may be provided to retard oxidation and deterioration of the tretinoin, thus providing the formulation with increased long term stability. The antioxidant used must be safe for human topical use and non-reactive to the other components of the formulation. A preferred example of a suitable antioxidant is butylated hydroxytoluene (BHT).

A preservative may be included in the formulation of the present invention to prevent microorganism overgrowth with time. In the present formulations, sorbic acid and imidazolidinyl urea have been used, although any preservative known by those skilled in the art and not otherwise deleterious to the formulation may be used.

A surfactant may also be provided in the formulation of the present invention to allow good dispersion of the active ingredient and to enhance skin penetration. In general, non-ionic surfactants should be employed, although their choice is not critical. In the example below, octoxynol-9 (polyethylene glycol mono[p-(1,1,3,3-tetramethylbutyl) phenyl]ether) was utilized with effectiveness.

Other humectants, such as glycerin, may also be provided to enhance the moisturizing capability of the present formulation.

In one embodiment of the invention, the tretinoin is present from about 0.001 to about 1% by weight, the gelling agent is present from about 0.05 to about 15% by weight, the proteinaceous material is present from about 0.001 to about 50% by weight, and the water is present from about 35 to about 95% by weight. In another embodiment, an antioxidant is present from about 0.001 to about 0.5% by weight, a preservative is present from about 0.001 to about 15% by weight, a surfactant is present from about 0.001 to about 2% by weight, and glycerine is present from about 1.0% to about 50% percent by weight.

The following example is presented to further illustrate a formulation of the invention without thereby limiting the scope thereof:

EXAMPLE OF A 0.05% TRETINOIN FORMULATION

|  | % w/w |
| --- | --- |
| Glycerin | 10.0 |
| Soluble Animal Collagen | 8.0 |
| Hydrolyzed Elastin | 1.0 |
| Triethanolamine | 0.58 |
| Carbomer 940 | 0.40 |
| Imidazolidinyl Urea | 0.364 |
| Sorbic Acid | 0.208 |
| Octoxynol-9 | 0.115 |
| Tretinoin USP | 0.05 |
| Butylate Hydroxytoluene (BHT) | 0.0208 |
| Sodium Hyaluronate | 0.011 |
| Purified Water | 79.2 |

The formulations of the present invention are prepared by a number of procedures well known in the art. For instance, the formulation of the above Example was prepared by first adding small portions of Carbomer 940 to heated purified water under low shear agitation until solvation occurred. Sorbic acid, BHT and imidazolidinyl urea were then mixed with the Carbomer 940/water mixture until dispersed. Then the glycerin and octoxynol-9 were added and mixed to form a homogeneous solution. The solution was then allowed to cool to room temperature and tretinoin added. Sodium hyaluronate was first dissolved in purified water and then added to the solution containing tretinoin. The collagen and elastin were then added and mixed until homogeneous. Finally, the triethanolamine was slowly added while mixing until a gel formed and the proper consistency and pH were achieved.

To stabilize the acidic carboxy polymer Carbomer 940, the pH of the formulation must be maintained between approximately 5.2 and approximately 5.5. Since pH will change as the percentage of tretinoin changes with different formulations, it may be necessary to use a neutralizing agent to bring the pH within the desired range. For instance, in formulations similar to that of the above Example, pH may be adjusted by varying the amount of the neutralizing agent triethanolamine.

The resulting formulation, therefore, is a stable, oil- and fat-free, alcohol-free, and potentially moisturizing vehicle for tretinoin. The formulation may be employed in virtually all instances where topical application of tretinoin is desired.

What is claimed is:

1. A stable aqueous gel formulation comprising:
   a) from about 0.001% to about 1% by weight tretinoin;
   b) from about 0.05% to about 15% by weight of a gelling agent for uniformly delivering said tretinoin to the surface of the skin in a way which makes it readily absorbable;
   c) from about 0.001% to about 50% by weight of a proteinaceous material, wherein said proteinaceous material comprises a protein, polypeptide, amino acid, mucopolysaccharide, or a mixture thereof, wherein said proteinaceous material is in sufficient quantity to stabilize said gelling agent and tretinoin formulation; and
   d) water;

wherein said formulation is free of fat and oil and substantially free of alcohol as a carrier for the tretinoin, said weight percentages being based on 100 weight percent of the formulation, and wherein said formulation is a stable aqueous gel.

2. The formulation of claim 1, wherein said tretinoin is present from about 0.001% to about 0.5% by weight.

3. The formulation of claim 1, wherein said tretinoin is present at approximately 0.05% by weight.

4. The formulation of claim 1, wherein the gelling agent is an acidic carboxy polymer which is partially neutralized with a neutralizing agent so as to maintain the pH of said formulation between approximately 5.2 and approximately 5.5.

5. The formulation of claim 1, and further comprising an antioxidant.

6. The formulation of claim 1, and further comprising a preservative.

7. The formulation of claim 1, and further comprising a surfactant.

8. The formulation of claim 1, and further comprising glycerin.

9. The formulation of claim 1, wherein said water is present from about 35 to about 95% by weight.

10. The formulation of claim 1, wherein the formulation comprises substantially no organic solvent so that the tretinoin remains substantially in suspension.

11. The formulation of claim 1, wherein the proteinaceous material comprises collagen, elastin, or sodium hyaluronate.

12. The formulation of claim 1, wherein the gelling agent is water soluble.

13. A stable aqueous gel formulation comprising:
 a) from about 0.001% to about 1% by weight tretinoin;
 b) from about 0.05% to about 15% by weight of an acidic carboxyl polymer gelling agent for uniformly delivering said tretinoin to the surface of the skin in a way which makes it readily absorbable;
 c) from about 0.001% to about 50% by weight of a proteinaceous material, wherein said proteinaceous material comprises a protein, polypeptide, amino acid, mucopolysaccharide, or a mixture thereof, wherein said proteinaceous material is in sufficient quantity to stabilize said acidic carboxyl polymer and tretinoin formulation; and
 d) water;
wherein the pH of said formulation is between approximately 5.2 and approximately 5.5 and wherein said formulation is free of fat and oil and substantially free of alcohol as a carrier for the tretinoin, said weight percentages being based on 100 weight percent of the formulation, and wherein said formulation is a stable aqueous gel.

14. The formulation of claim 13, wherein said tretinoin is present from about 0.001% to about 0.5% by weight.

15. The formulation of claim 13, wherein said tretinoin is present at approximately 0.05% by weight.

16. The formulation of claim 13, wherein said acidic carboxy polymer is partially neutralized with an organic amine.

17. The formulation of claim 13, and further comprising an antioxidant.

18. The formulation of claim 13, and further comprising a preservative.

19. The formulation of claim 13, and further comprising a surfactant.

20. The formulation of claim 17, and further comprising glycerin.

21. The formulation of claim 13, wherein the proteinaceous material comprises collagen, elastin, or sodium hyaluronate.

22. The formulation of claim 13, wherein said water is present from about 35 to about 95% by weight.

* * * * *